United States Patent [19]

Gibson

[11] Patent Number: 5,331,102
[45] Date of Patent: Jul. 19, 1994

[54] METHOD FOR DECOLORIZATION OF ALKANOLAMINES AND ALKYLENEAMINES

[75] Inventor: Charles A. Gibson, South Charleston, W. Va.

[73] Assignee: Union Carbide Chemicals & Plastics Technology Corporation, Danbury, Conn.

[21] Appl. No.: 83,663

[22] Filed: Jun. 28, 1993

[51] Int. Cl.$^5$ .................................... C07C 209/84
[52] U.S. Cl. .................................. 564/498; 564/469; 564/470; 564/478; 564/479; 564/480; 564/503; 564/511; 564/512
[58] Field of Search ........... 564/498, 497, 503, 511, 564/512, 478, 479, 480, 469, 470

[56] References Cited

U.S. PATENT DOCUMENTS

| | | | |
|---|---|---|---|
| 2,744,938 | 5/1956 | Urban et al. | 260/613 |
| 3,207,790 | 9/1965 | Glew et al. | 260/584 |
| 3,217,026 | 11/1965 | Vertnik et al. | 564/498 |
| 3,453,183 | 7/1969 | Okubo | 203/33 |
| 3,723,529 | 3/1973 | Pitts et al. | 260/583 N |
| 3,819,710 | 6/1974 | Jordan | 260/584 R |
| 4,570,019 | 2/1986 | Gibson et al. | 564/498 |
| 4,731,165 | 3/1988 | Niebruegge et al. | 203/29 |
| 4,737,243 | 4/1988 | Siml et al. | 203/29 |
| 4,827,037 | 5/1989 | Doumaux, Jr. | 564/498 |
| 4,970,344 | 11/1990 | Keller | 564/497 |
| 5,019,653 | 5/1991 | Speranza et al. | 564/497 |

FOREIGN PATENT DOCUMENTS 0477593 1/1992 European Pat. Off. .
1351050 12/1971 United Kingdom .

OTHER PUBLICATIONS

Derwent Abstract 47683T, corresponding to Japanese Application 119,902 (1972).

Primary Examiner—Glennon H. Hollrah
Assistant Examiner—Scott C. Rand
Attorney, Agent, or Firm—R. M. Allen

[57] ABSTRACT

Color-containing alkanolamines or alkyleneamines, having color numbers of up to 100 PtCo or higher, can be treated with inorganic solid acidic catalysts. Inorganic support materials having bonded inorganic acid functionalities may be used as the inorganic solid acidic catalysts. In the presence of water, these inorganic solid acidic catalysts produce decolorized alkanolamines or alkyleneamines having color numbers of 20 PtCo or less. The process of decolorization can be carried out in batch or continuous mode processes thus providing low cost, high quality and high purity end products.

18 Claims, No Drawings

METHOD FOR DECOLORIZATION OF ALKANOLAMINES AND ALKYLENEAMINES

BACKGROUND OF THE INVENTION

The present invention relates to processes for decolorizing alkanolamines and alkyleneamines, and more particularly, to both batch and continuous processes for producing alkanolamines and alkyleneamines having improved color characteristics by treatment with solid acidic catalyst.

Price and purity are important characteristics of a chemical's marketability to a potential customer. During industrial processes used to produce various chemicals, impurities often enter the processes and manifest themselves in the form of color contamination. The sources of this color contamination may be metals and metal compounds from the catalysts or equipment used in the processes, or conjugated organic compounds which are formed during the processes. Since the mechanism by which these color contaminants are formed varies from process to process, the decolorization process normally acts by a mechanism which depends on the color source.

It is well known that alkyleneamines, particularly the higher polyamines, become discolored during their preparation which generally reduces their commercial value. Various procedures have been used commercially or suggested for decolorizing or otherwise improving the color of these compounds including, for example, treating with hydrogen chloride or amine hydrochlorides as disclosed in JA-119902, UK Pat. No. 1,351,050; treatment with activated carbon, acid treated clays or acidic zeolites at elevated temperatures (about 200° C.) as disclosed in U.S. Pat. Nos. 3,723,529 and 4,737,243; and treatment with a sulfonic acid ion exchange resin as disclosed in U.S. Pat. No. 4,731,165. In each of these procedures, distillation is generally a final step needed to achieve the desired color, and neutralization of residues, handling and disposal of acids, or reactivation of the treatment medium require special apparatus which complicate the processes.

U.S. Pat. No. 4,570,019 discloses a process which may be run continuously for producing polyalkylene polyamines having improved color characteristics which comprises treating discolored polyethylene polyamines with polyethylene polyamine hydrochloride in the presence of water at elevated temperatures, thus eliminating extra handling steps described in the processes above.

However, as is known in the art, methods used for decolorization of higher polyethylene polyamines are generally not transferable to compounds such as alkanolamines which are prepared by different processes and which use different reactants.

For example, alkanolamines may be conventionally prepared by reacting an alkylene oxide with ammonia or an amine, or, more particularly, alkanolamines such as aminoethylethanolamine may typically be prepared by the reductive amination of monoethanolamine.

Alkanolamines produced by these conventional processes can vary in color from nearly colorless water-white liquids to pale yellow. Alkanolamines, particularly ethanolamines, are susceptible to color formation in the presence of oxygen (e.g. from air leaks during manufacture and/or storage), excessive temperature and soluble metals such as iron or nickel. Also, impurities in raw materials may contribute to the initial and continuing formation of color bodies.

Various attempts to overcome the problems associated with color and color instability of alkanolamines have proven to be cost intensive and environmentally unacceptable. Such attempts have included purification by fractional distillation, concentration of color forming bodies or their precursors by fractional distillation, carbon treatment, the use of adsorbent materials, various hydrogenation techniques, and the use of reducing agents such as sodium borohydride and hydrazine.

U.S. Pat. No. 2,744,938 describes a process for the treatment of color-sensitive organic compounds which have become discolored through oxidation or upon aging. The patent specifically describes the method of removal of color bodies from alkylphenols with a catalyst-free solid adsorbent in the presence of hydrogen maintained at super atmospheric pressure. The thus treated alkylphenol is then separated from the solid adsorbent material.

U.S. Pat. No. 3,207,790 describes a process for improving the color of alkanolamines that develop undesirable color on aging by adding a sufficient amount of a borohydride of an alkali metal. The borohydrides have appreciable solubility in the alkanolamines and after dissolution, may remain in the solution or the alkanolamines may be distilled under reduced pressure.

U.S. Pat. No. 3,453,183 describes a method of removing aldehyde impurities from ethanolamines by forming a mixture of the ethanolamines with either powdered silicas, powdered silicates, liquid silicates or powdered aluminas, followed by separation of the ethanolamines by vacuum distillation.

U.S. Pat. No. 3,819,710 describes a process for improving color and color stability of ethanolamines by hydrogenation using selected catalysts and selected catalysts conditions. Useful catalysts for the process include Raney nickel, platinum, palladium or ruthenium.

EP 0477593 describes purification and decolorization of off-color crude N-dialkyl dialkanolamines by vacuum distilling in the presence of water and a water-soluble metal borohydride.

The above patents confirm the need for methods of improving the color characteristics of both alkanolamines and alkyleneamines. While some of the processes such as the use of solid adsorbents results in improved color, such processes are not entirely suitable for large scale decolorization and require labor intensive steps for recovery of the desired product adding expense to the process in terms of time of treatment, equipment costs, and disposal of byproducts.

Other methods, such as hydrogenation of color impurities requires expensive Raney nickel which must be replaced on a regular schedule. Hydrogenation systems also require special equipment for hydrogen supply, mixing and, after reduction, filtration to remove the Raney nickel, since distillation in the presence of Raney nickel tends to generate color and deactivate the catalyst.

The need exists for an inexpensive easily operated process of producing alkanolamines or alkyleneamines having reduced color.

SUMMARY OF THE INVENTION

In accordance with the present invention there is provided a method of producing alkanolamines or alkyleneamines having reduced color comprising contacting color-containing alkanolamines or alkyleneamines with inorganic solid acidic catalysts in the presence of water, for a time sufficient to reduce the color of the alkanolamines or alkyleneamines. Preferably the decolorization step is carried out under pressures high enough to maintain water in the liquid phase.

The heterogeneous catalysts used in accordance with the present invention, advantageously provide versatility in allowing both batch and continuous processing of the color-containing alkanolamines or alkyleneamines. The processes may readily be incorporated into typical manufacturing facilities, providing low cost, high quality and high purity end products.

The methods of the invention may effectively treat color-containing alkanolamines or alkyleneamines with colors up to a Platinum-Cobalt (PtCo) number of 100 or higher to obtain products with reduced color numbers of about 20 PtCo or less.

DESCRIPTION OF THE PREFERRED EMBODIMENTS

The discolored alkanolamines or alkyleneamines to which the present invention relates can be prepared by any of the processes well known in the art such as where a crude mixture is produced and then subjected to refining procedures where desired individual components or mixtures thereof are separated and recovered. The products recovered by the various refining or separation processes are, in general, discolored, having PtCo numbers ranging from up to 700 or greater, as determined using ASTM Method 1209 "Color of Clear Liquids (Platinum-Cobalt Scale)."

In the absence of any preotreatment, refined alkanolamines, such as for example aminoethylethanolamine (AEEA), may have color numbers being close to about 60 PtCo or higher.

In addition, alkanolamines or alkyleneamines which may have been treated previously by other known decolorization methods, some of which may have lower color numbers initially, upon storage become discolored due to increases in storage temperatures, exposure to air or metal contamination from the storage container.

The following description of the preferred embodiments will refer to decolorization of alkanolamines, in particular AEEA. However, the scope is intended to include both alkanolamines and alkyleneamines, as it has been surprisingly found that the present invention may be applicable to both types of compounds as evidenced by the Examples.

Color impurities found in alkanolamines may be removed by contacting color-containing alkanolamines with solid acidic catalysts. Suitable solid acidic catalysts for use in the practice of the invention include compounds prepared by treating an inorganic support material with inorganic acids, or compounds which provide inorganic acid functionalities in situ, which bond to the support material.

Suitable inorganic support materials include metal oxides, various aluminas, silicas, and mixtures thereof. A preferred inorganic support material for the preparation of solid acidic catalysts are metal oxides including oxides selected from the group consisting of titanium, zirconium, vanadium, chromium, manganese, iron, cobalt, aluminum and silicon. Preferred metal oxides include zirconium oxide and aluminum oxide. Mixed metal oxides may also be used in preparing solid acidic catalysts and include for example, $TiO_2/Al_2O_3$, $TiO_2/SiO_2$, $SiO_2/Al_2O_3$ and $ZrO_2/Al_2O_3$.

Aluminum oxides, in particular activated aluminas, comprise a preferred class of supports, and are a series of partially hydroxylated aluminum oxides. In general, as a hydrous alumina precursor is heated, hydroxyl groups are driven off leaving a porous solid structure of activated alumina. This controlled heating or calcining process results in a series of transitional aluminas or activated aluminas. Of the activated aluminas described above, gamma aluminas are preferred since the higher surface area, generally 100–300 $m^2/gm$ or higher, provides increased sites for acidity.

The term "support," as used herein and in the claims, means a solid structure which does not unduly adversely affect the catalytic properties of the catalyst and is at least as stable as the catalyst to the reaction medium.

Although some of the support materials used may have acidic characteristics, such as silicas and silica-aluminas, it has been found that these types of acidic support materials alone are not sufficient to decolorize alkanolamines or alkyleneamines and instead, may contribute to the formation of color bodies when they are not part of the solid acid catalyst structure of the present invention.

The solid acidic catalyst is prepared by treating the inorganic support material with inorganic acids, or compounds which provide inorganic acid functionalities in situ, which bond to the support material. The preferred sources of acidity include compounds which provide fluoride, chloride and sulfate ions capable of bonding to the inorganic support material. For example, hydrogen fluoride, ammonium bifluoride, sulfuric acid, hydrochloric acid and the like may be used to provide the inorganic acid functionalities used to produce the solid acidic catalysts. A most preferred source of acidity is ammonium bifluoride. It is believed that it is the high electronegativity of the fluoride ion which provides a stable, reproducible catalyst which does not deleteriously leach when contacted with aqueous amines.

Numerous conventional methods of vapor-phase fluorination and impregnation exists for fluorinating support materials such as metal oxides. In one type of vapor-phase fluorination, the metal oxide is maintained in contact with vapors of fluorine-containing compounds such as $F_2$, HF, $BF_3$, $SbF_5$, $NH_4F$, $CF_4$, $CHF_3$, $CH_2F_2$, $CF_3COOH$, $CF_3OH$, $CF_3OCF_3$, $CF_3CH_2OH$, $SF_6$, $SO_2F_2$ or $SOF_2$ at an elevated temperature, usually at a temperature between 100° and 500° C.

Another method of preparing fluorinated solid acidic catalysts may be by impregnation, carried out by saturating the catalyst, usually at room temperature, with an aqueous solution containing an appropriate amount of a compound such as HF, $BF_3$, $HBF_4$, $NH_4F$, $NH_4HF_2$, $NH_4BF$ or $NH_4SiF_6$. The impregnated catalyst may then be dried at 100° C. in vacuum and calcined at higher temperatures ranging from about 300° C. to about 700° C.

When treating color-containing alkanolamines or alkyleneamines, the amount of catalyst used depends on the concentration and strength of the acid functionality. Generally in a batch mode operation, from about 0.1 to 30 percent by weight of the solid acidic catalyst is used based on the weight of material to be treated. For example, when using an alumina treated support containing 3 to 8 percent by weight of fluoride, the amount of catalyst used is preferably 10 to 15 percent by weight of the material to be treated.

It is believed that higher acid concentrations and strengths facilitate the rate of decolorization. However, extensive fluorination may be regressive due to a decrease in available surface area, resulting in lower acid strength (i.e. number of Brönsted sites) above the 10% level of fluorination. Thus, the useful inorganic acid concentrations are from about 0.1% to 10%, preferably 1% to 6%, and more preferably 4 to 6% of the weight of the support material.

The acid concentration and strength may be determined by methods known in the art such as non-aqueous amine titration (Hammett and arylmethanol indicators), infrared spectroscopy, differential thermal analysis, gaseous adsorption and the like. In addition, methods such as ion chromatography or specific ion electrode methods provide a means of analyzing acid solutions before and after contact with the support material to determine acid concentration on the final catalyst.

Increased surface area of the catalyst may aid in increasing activity of the catalyst relative to fluoride content. Thus, a preferred catalyst structure comprises an inorganic support material having a surface area from about 50 m$^2$/gm to about 340 m$^2$/gm or greater and an inorganic acid concentration of from about 4% to about 6%.

Without intending to be bound by any particular theory, it is believed that in the presence of water, strong protonic acid sites exist on solid acidic catalysts such as fluorinated alumina which may not have been observed on untreated aluminas. The amount of water present is generally in the range of 1 to 10 percent, preferably 3 to 8 percent and most preferably 4 to 6 percent by weight of the material to be decolorized.

The above described solid acidic catalysts may reduce color during initial use without water, however, the degree of color reduction and stability of the decolorized product is less and the process may not be adaptable for continuous use processes. Further, anhydrous processes may contribute to deactivation of the catalyst due to the accumulation of heavy byproducts which may form during the color removal step.

The process may be run over a wide ranges of temperatures from about 150° to 250° C. Preferably, the temperature range is from about 190° to 220° C., and most preferably from about 205° to about 210° C. The pressure of the system should be high enough to assure retention of water in the liquid phase, and is normally in the range of 1–100 psig, more preferably 20–75 psig, and most preferably 50–65 psig.

In a typical embodiment, the process of the present invention may be carried out in both batch and continuous modes. In the batch mode, treated product is discharged and fresh product, to be treated, is added. The catalyst may conveniently be maintained in the reactor by use of a basket made of porous screens. In a batch mode operation, the use of agitation may be beneficial in improving catalyst efficiency. Typical means of agitation include the use of mechanical stirrers at speeds ranging from about 400 to about 1200 rpm.

In a continuous mode of operation, a fixed catalyst bed may be used and product to be treated pumped through the bed. In such a continuous process, water is typically introduced as makeup and normal distillation is used to provide low color and color stable products. The amount of catalyst used depends on the design of the process equipment, acid concentration and strength, and process conditions, as is known in the art. Although the mechanism of decolorization is not completely understood, it is believed that during a continuous process, color formers are destroyed during the process and become light fragments which are removed during distillation or heavy fragments which go out with the residue stream.

The color-containing alkanolamines or alkyleneamines should be in contact with the solid acidic catalyst for a time sufficient to produce a decolorized product. Typically, the residence time for either batch or continuous modes of operation may be up to about 8 hours, preferably about 4 to 6, and most preferably about 4 to 5 hours. The length of time for decolorization depends on the acid concentration and strength of the catalyst, temperature, and amount of water present in the system as illustrated by the following examples.

EXAMPLES

A sample of refined AEEA having an initial color number of from about 50.0 PtCo was used in Examples 1–8. The reaction system for evaluating the solid acidic catalyst consisted of a 4-neck, 500 ml flask equipped with an addition funnel, a thermometer, a stirrer and an 18 inch by ¾ inch column with a distillation head. A slight back pressure was maintained on the system equivalent to about 20 inches of water (0.72 psig). The distillation equipment was typically the same as the reaction equipment.

EXAMPLE 1

Preparation of Sulfate-Bound Zirconium Oxide

A total of 64.5 grams (0.2 mole) of zirconyl chloride ($ZrOCl_2 \cdot 8 H_2O$), obtained from Fisher Scientific Company, is dissolved in 1 liter of distilled deionized water and zirconium hydroxide is precipitated by adding 40 ml of concentrated (17N) ammonium hydroxide. The mixture is stirred at room temperature for 45 minutes, filtered, washed with 100 ml of distilled water (4×) and placed in a 110° C. oven overnight. A total of 31 grams of zirconium hydroxide hydrate is obtained. This material is then placed in a Büchner funnel under vacuum and treated with 407 ml of aqueous 1N sulfuric acid. After air drying, the material is placed in a Pyrex tube and calcined in air at 575° C. for 3 hours. A total of 28.8 grams of sulfate-bound zirconium oxide catalyst is obtained.

EXAMPLE 2

Control

AEEA, 250 grams, and 20 grams of distilled, deionized water are charged to the reaction system described above. The materials are stirred and heated at 204° to 212° C. for 4 hours. After the reaction period and cooling, the system is placed under vacuum and water removed overhead to cold traps. The distillation is continued and a first distillate fraction of 62 grams, containing residual water and possibly hydrolyzed fragments of color forming bodies, is removed to a head temperature of 93° C., 3 mm Hg pressure (0.058 psia). A second fraction, 160 grams untreated AEEA, is removed at a head temperature of 82° C., 2 mm Hg pressure (0.039 psia). The second fraction of untreated AEEA has a color of 60.0 PtCo.

EXAMPLE 3

Decolorization of AEEA

AEEA, 250 grams, along with 10 grams distilled, deionized water and 1 gram of the sulfate-bound zirconium oxide catalyst of Example 1 are charged to the reaction system described in Example 2. The mixture is stirred and heated at 205° to 212° C. for 4 hours and then cooled. The distillation is continued and a first distillate fraction of 49.5 grams, containing residual water and possibly hydrolyzed fragments of color forming bodies, is removed at a head temperature of 81° C., 3 mm Hg. A second distillate fraction, 165 grams of AEEA, is removed at a head temperature of 86° C., 3 mm Hg, with a reflux ratio of one to one. The second distillate fraction (treated AEEA) has a color of 20.0 PtCo.

EXAMPLE 4

A total of 215 grams of AEEA and 20 grams of distilled, deionized water are charged to the 35 grams of residual material which contains the solid acidic catalyst from Example 3. The mixture is stirred and heated at 202° C. to 211° C. for 4 hours then cooled. The system is placed under vacuum and water removed overhead to cold traps. The distillation is continued and a first distillate fraction of 50 grams is removed at a head temperature of 86° C., 3 mm Hg. A second distillate fraction, 157 grams of AEEA, is removed at a head temperature of 87° C., 3 mm Hg, with a reflux ratio of one to one. The color of the treated AEEA, is 20.0 PtCo.

EXAMPLE 5

AEEA, 215 grams, 30 grams of distilled, deionized water, and 1 gram of the zirconium catalyst of Example 1 are added to the reaction flask which contained residue and catalyst from Example 4 resulting in a total of 2 grams catalyst. The mixture is stirred and heated at 204° to 208° C. for 4 hours then cooled. The system is placed under vacuum and water removed overhead to cold traps. The distillation is continued and a first distillate fraction of 45.7 grams removed at 84° C., 3 mm Hg. A second distillate fraction, 158.2 grams AEEA, is removed at 91° C., 2 mm Hg, with a reflux ratio of one to one. The color of the treated AEEA, is 10.0 PtCo.

EXAMPLE 6

A total of 30.5 grams of the supernatant liquid and the solid acidic catalyst from Example 5 is decanted from the reaction flask. The supernatant liquid and solid catalyst are diluted with two volumes of methanol and filtered to recover 0.9455 grams of the zirconium catalyst. AEEA, 240 grams, 15 grams distilled, deionized water and 0.3164 grams of fresh zirconium catalyst are charged to the remaining solid acidic catalyst from Example 5, resulting in a total catalyst amount of about 1.3 grams of solid acidic catalyst. The reaction mixture is stirred and heated for 4 hours at 208° C. then cooled. The system is placed under vacuum and water removed overhead to cold traps. The distillation is continued and a first distillate fraction of 35.2 grams removed at 82° C., 3 mm Hg with a reflux ratio of one to one. The second distillate fraction, 152.8 grams AEEA, is removed at 90° C., 3.5 mm Hg. The color of the treated AEEA, is 20.0 PtCo.

EXAMPLE 7

AEEA, 215 grams, 15 grams distilled, deionized water, and 1.10 grams of the zirconium catalyst of Example 1 are charged to the residual kettle material remaining from Example 6, resulting in a total amount of 2.4 grams of catalyst. The mixture is stirred and heated for 4 hours at 207° to 209° C. and then cooled. The system is placed under vacuum and water removed overhead to cold traps. The distillation is continued and a first distillate fraction of 44.2 grams removed at a head temperature of 87° C., 3 mm Hg. A second distillate fraction, 157.3 grams AEEA, is removed at a head temperature of 94° C., 4 mm Hg with a reflux ratio of one to one. The color of the treated AEEA is 10.0 PtCo.

EXAMPLE 8

An additional 215 grams of untreated AEEA and 15 grams of water are charged to the residual material from Example 7. The mixture is stirred and heated to 205° to 208° C. for 4 hours then cooled. The system is placed under vacuum and water removed overhead to cold traps. The distillation is continued and a first distillate fraction of 40 grams removed at a head temperature of 84° C., 3.5 mm Hg. A second distillate fraction, 176 grams AEEA, is removed at a head temperature of 92° C., 4 mm Hg, with a reflux ratio of one to one. The color of the treated AEEA is less than 10.0 Pt Co.

EXAMPLE 9

Preparation of 2% Aluminum Fluoride Catalyst

Twenty grams of gamma alumina, high surface area, 1/16" extrudate (LA 6173) obtained from Norton Chemical Company is placed in a filter flask equipped with a rubber stopper and septum and evacuated. A solution containing 14.8 grams of distilled, deionized water and 0.8 grams of 48% HF solution (Mallinckrodt, Inc.) is loaded to a plastic syringe and added to the flask containing the alumina. The vacuum is released and the mixture allowed to stand for 30 minutes. The solid acidic catalyst is transferred to a dish and dried overnight in an oven at 100° C. in air, followed by calcining in air at 500° C. for 4 hours. The solid acidic catalyst has a surface area of 207 $m^2$/gm. The amount of fluoride reacted and the original weight of gamma alumina provided the basis for determining the percent fluoride level on the final catalyst. For example, in the present example, 0.4 grams HF and 20.0 grams of support material will yield a 2% fluoride-containing catalyst.

Examples 10–21 were run using refined AEEA having an initial color number of about 46.5 PtCo. The reaction system for evaluating the above catalyst was an autoclave equipped with an agitator, nitrogen pressure regulator and temperature controller. Distillation equipment consisted of a 3 tray Oldershaw column having 1 inch tray spacings, equipped with a distillation head.

EXAMPLE 10

Control

AEEA, 600 grams, and 6 grams of distilled water are charged to a 2-liter stainless steel autoclave. The autoclave is purged with nitrogen and pressurized to 55 psig. The agitator is adjusted to between 400 and 600 rpm and the autoclave heated to 205°–207° C. for 4 hours at a regulated pressure of 55 psig. The reactor contents are cooled to 25° C. and discharged to the distillation column described above. A total of 585 grams of distillate is removed at a temperature of 87° C., pressure of 3 mm Hg and a reflux ratio of 2:1. The untreated AEEA distillate has a color of 40.9 PtCo.

EXAMPLE 11

Duplicate Control

The conditions of Example 10 are repeated with the same starting materials. The untreated AEEA distillate has a color of 46.5 PtCo.

EXAMPLE 12

Decolorization of AEEA

A total of 600 grams of AEEA of the same quality used in Example 10 and 7.3 grams of distilled, deionized water are charged to the equipment used in Example 10. Six grams of a two percent by weight HF on alumina catalyst, prepared by the method of Example 9, dried at 100° C. and calcined at 500° C. for 4 hours in air, is added to the mixture of AEEA and water. The autoclave is heated to 205°–206° C. for 4 hours. The HF on alumina catalyst of Example 9 is located in a ⅝ inch diameter by 6 inch long stainless fine mesh steel screen basket attached to an internal baffle. After cooling, the reaction product is removed from the autoclave and distilled under the conditions of Example 10. The distillate, 525 grams of decolorized AEEA, has a color of 34.0 PtCo.

The following additional examples were run using the equipment and procedures of Example 10 and the catalyst of Example 9:

| Example No. | AEEA (gms) | Water (gms) | Catalyst (alumina) | Color (PtCo) |
| --- | --- | --- | --- | --- |
| 13 | 600 | 30 | 2% HF | 16.1 |
| 14 | 600 | 30 | 2% HF | 20.6 |

EXAMPLE 15

Preparation of 6% Aluminum Fluoride Catalyst

A second solid acidic catalyst is prepared by treating about 560 grams of a high surface area gamma alumina, obtained from Norton Chemical Company, with one liter of 1M aqueous ammonium bifluoride, drying at 100° C. and calcining at 500° C. for 4 hours. The HF addition to the alumina was approximately 6 weight percent as determined by the amount of fluoride adsorbed on the alumina support. The fluoride weight was determined by the amount of fluoride in the 1M aqueous ammonium bifluoride solution used relative to the weight of gamma alumina.

The following examples were run using the above prepared catalyst and the equipment and conditions of Example 10. This process simulates performance of the catalyst under continuous process conditions.

| Example No. | AEEA (gms) | Water (gms) | Catalyst (Alumina) | Color (PtCo) |
| --- | --- | --- | --- | --- |
| 16 | 600 | 30 | 6% HF (60 grams) | 14.6 |
| 17 | 600 | 30 | Ex. 16 (recycled) | 11.2 |
| 18 | 600 | 30 | Ex. 17 (recycled) | 33.0 |
| 19 | 600 | 30 | Ex. 18 (recycled) | 16.1 |

-continued

| Example No. | AEEA (gms) | Water (gms) | Catalyst (Alumina) | Color (PtCo) |
| --- | --- | --- | --- | --- |
| 20 | 600 | 30 | Ex. 19 (recycled) | 16.0 |
| 21 | 600 | 30 | Ex. 20 (recycled) | 6.7 |
| 22 | 600 | 30 | Ex. 21 (recycled) | 9.2 |

A sample of silica-alumina (75% $SiO_2$, 25% $Al_2O_3$, obtained from Davison-Grace) is used to compare the effectiveness of an untreated inorganic support material for removing color from untreated AEEA in the following example.

EXAMPLE 23

Comparative Example

Blank 250 g of AEEA, PtCo 79.5, and 10 grams of distilled water are charged to a stirred, one-liter flask equipped with a five trayed Oldershaw column (1-inch diameter), a distillation head and a vacuum source. The system is placed under a slight positive pressure and heated to 209° C. for 3 hours with agitation under a nitrogen atmosphere. The system is cooled and placed under a pressure of 2 mm Hg. A 201 gram AEEA distillate fraction is removed and has a color number of 53 PtCo.

Untreated Support

A sample of 250 grams untreated AEEA and 10 grams of distilled water is placed in the equipment described above. The untreated silica-alumina support material, 2.5 grams, is charged to the stirred flask and the system heated to 205°–208° C. for 3.5 hours. The system is cooled and the silica-alumina pellets removed. After placing the system under a pressure of 1.8 mm Hg, a 208 gram treated AEEA distillate is removed and has a color number of 61.5 PtCo.

Although silica-aluminas demonstrate both Brönsted (protonic) and Lewis acid sites and have sufficiently high surface areas, the support materials alone may not be active solid, acidic catalyst for removal of color as used in the present invention.

The following examples show the decolorization of an alkyleneamine, triethylenetetramine (TETA), using the process of the present invention. The original untreated crude TETA has a color of 131 PtCo.

EXAMPLE 24

Preparation of 4% Aluminum Fluoride Catalyst

A 200 gram sample of spherical alumina (A-202) having a surface area of 340 $m^2/g$, obtained from LaRoche Chemical Company, is mixed with an aqueous solution containing 250 grams water and 15.12 grams of 98% pure ammonium bifluoride (Aldrich Chemical Co.) at ambient temperature for one hour. The fluoride content of the final catalyst is determined by analyzing both the starting solution and the final supernatant solution using ion chromatography. The original solution assayed 3.71 percent fluoride ion and the final supernatant solution assayed 0.5 percent fluoride ion, yielding a 4% aluminum fluoride catalyst. The catalyst is dried at 100° C. in vacuum and calcined for 4 hours at 500° C. in air prior to use.

Examples 25 and 26 were run using an autoclave equipped with an agitator, nitrogen pressure regulator and temperature controller. Distillation equipment consisted of a 5 tray Oldershaw column having 1 inch tray spacings, equipped with a distillation head.

EXAMPLE 25

Control

TETA, 400 grams, is charged to the distillation equipment described above. A first distillate fraction of 26 grams is removed at a head temperature of 128° C., pressure of 4 mm Hg and a reflux ratio of five to one. A second distillate fraction, 301 grams untreated TETA, is removed at 135° C., pressure of 4 mm Hg and a reflux ratio of one to one. The second distillate fraction of untreated TETA has a color of 433 PtCo.

EXAMPLE 26

Color Stabilization of Crude TETA

A total of 600 grams of TETA and 30 grams of water are charged to the autoclave reaction equipment described above containing 60 grams of catalyst prepared in Example 24. The autoclave system was operated in the same manner describe in Example 10 above. After cooling, the TETA-water mixture is removed from the autoclave and fractionated in the distillation equipment. A first distillate fraction of 49.3 grams is removed at a head temperature of 131° C., 4 mm Hg and a reflux ratio of five to one. The second distillate fraction, 448.2 grams treated TETA, is removed at a head temperature of 137° C., 4 mm Hg with a reflux ratio of one to one. The color of the treated TETA is 204 PtCo.

The experimental procedure is repeated using a 60 grams of a second fluorinated alumina catalyst prepared by the process of Example 24 except calcined at 600° C. The treated TETA distillate, 458.5 grams, has a color of 202 PtCo.

EXAMPLE 27

Additional Treatment of TETA

The distillate fractions from Example 26 (497.5 grams total) are combined and again treated in the autoclave with 5% water and 60 grams of a fluorinated alumina catalyst (6%) which has been calcined at 600° C. Fractional distillation of the treated TETA using the column described above results in a TETA distillate fraction, 376 grams, having a color of 69 PtCo.

A sample of untreated refined TETA having an initial PtCo color of 87.5 was used in the following examples.

EXAMPLE 28

Control

TETA, 231 grams, is fractionated using the distillation equipment of Example 25. The second distillate fraction, 186 grams untreated TETA, is removed at 135° C., 4 mm Hg, and has a color of 185.9 PtCo.

EXAMPLE 29

Decolorization of Refined TETA

TETA, 600 grams, and 30 grams of water are charged to the autoclave equipment of Example 26, containing 60 grams of a 4% aluminum fluoride catalyst prepared by the procedure of Example 24. The autoclave is operated at 205°–207° C. for 4 hours with 1200 rpm agitation. After cooling, the treated TETA is fractionated in the distillation equipment to yield a second distillate fraction, 506 grams treated TETA, having a color of 44.4 PtCo.

What is claimed is:

1. A method of producing alkanolamines or alkyleneamines having a reduced color comprising contacting, in the presence of water, color-containing alkanolamines or alkyleneamines with a solid acid catalyst comprising a metal oxide having a bonded inorganic acid functionality selected from the group consisting of chloride, fluoride, and sulfate ions, under conditions effective to reduce the color of said alkanolamines or alkyleneamines.

2. The method of claim 1 wherein said inorganic support material is selected from the group consisting of aluminum oxide and zirconium oxide.

3. The method of claim 1 wherein said inorganic support material is gamma alumina.

4. The method of claim 1 wherein said inorganic support material has a surface area greater than 100 m$^2$/gm.

5. The method of claim 1 wherein said inorganic acid functionality is provided by a compound selected from the group consisting of hydrogen fluoride, ammonium bifluoride, sulfuric acid and hydrochloric acid.

6. The method of claim 1 wherein said inorganic acid functionality is provided by ammonium bifluoride.

7. The method of claim 1 wherein said inorganic acid functionality is in a concentration ranging from about 0.1 to 10 percent by weight of the support material.

8. The method of claim 7 wherein said inorganic acid functionality is in a concentration ranging from about 1 to 6 percent by weight of the support material.

9. The method of claim 7 wherein said inorganic acid functionality is in a concentration ranging from about 4 to 6 percent by weight of the support material.

10. The method of claim 2 wherein said solid acidic catalyst has been calcined at a temperature of from about 300° C. to about 700° C.

11. The method of claim 1 wherein water is present in a concentration of from about 1 to about 10 percent by weight of the alkanolamine or alkyleneamine.

12. The method of claim 1 wherein water is present in a concentration of from about 4 to about 6 percent by weight of the alkanolamine or alkyleneamine.

13. The method of claim 1 wherein said alkanolamines having reduced color have a color number of 20 PtCo or less.

14. The method of claim 1 wherein said alkanolamines having reduced color have a color number of 10 PtCo or less.

15. A method of producing aminoethylethanolamine having a reduced color comprising contacting, in the presence of water, color-containing aminoethylethanolamine with a solid acidic catalyst comprising an alumina support material having a bonded fluoride acid functionality, under conditions effective to reduce the color of said aminoethylethanolamine.

16. The method of claim 15 wherein said aminoethylethanolamine having a reduced color has a color number of 10 PtCo or less.

17. A method of producing triethylenetetramine having a reduced color comprising contacting, in the presence of water, color-containing triethylenetetramine with a solid acidic catalyst comprising an alumina support material having a bonded fluoride acid functionality, under conditions effective to reduce the color of said triethylenetetramine.

18. The method of claim 17 wherein said triethylenetetramine having a reduced color has a color number of 50 PtCo or less.

* * * * *